(12) United States Patent
Shiffler

(10) Patent No.: US 6,557,778 B1
(45) Date of Patent: May 6, 2003

(54) TOUCHLESS VOLATILE DISPENSER

(75) Inventor: Benjamin N. Shiffler, Racine County, WI (US)

(73) Assignee: S. C. Johnson & Son, Inc., Racine, WI (US)

(*) Notice: Subject to any disclaimer, the term of this patent is extended or adjusted under 35 U.S.C. 154(b) by 0 days.

(21) Appl. No.: 09/536,975

(22) Filed: Mar. 28, 2000

(51) Int. Cl.7 .................................................. A24F 25/00
(52) U.S. Cl. ............................. 239/56; 239/54; 239/53; 239/55
(58) Field of Search ............................. 239/34, 44, 47, 239/48, 53, 54, 56, 55, 57

(56) References Cited

U.S. PATENT DOCUMENTS

| 668,640 A | | 2/1901 | Hahn |
|---|---|---|---|
| 960,527 A | | 6/1910 | Von Essen |
| 968,237 A | | 8/1910 | Dean |
| 1,769,409 A | * | 7/1930 | Armstrong |
| RE21,065 E | | 5/1939 | Copeman |
| 3,065,915 A | * | 11/1962 | Samann |
| 3,129,888 A | * | 4/1964 | O'Hagan |
| 3,770,199 A | * | 11/1973 | Hoek et al. |
| 4,749,082 A | * | 6/1988 | Gardiner et al. ........ 206/315.11 |
| 4,804,142 A | * | 2/1989 | Riley |
| 5,164,178 A | * | 11/1992 | Muysson |
| 5,170,886 A | * | 12/1992 | Holzner |
| 5,184,724 A | * | 2/1993 | Mayled ...................... 206/466 |
| 5,394,640 A | | 3/1995 | Musket |
| 5,590,785 A | * | 1/1997 | Seitzinger ................... 206/575 |
| 5,720,432 A | | 2/1998 | Gaskin ......................... 239/36 |
| 6,012,643 A | | 1/2000 | Barlow et al. |

FOREIGN PATENT DOCUMENTS

WO   WO97/20581 A1 * 6/1997

* cited by examiner

Primary Examiner—Christopher Kim

(57) ABSTRACT

Disclosed herein are strips for dispensing insecticidal actives and fragrances. The strips are stored in vapor impermeable pouches where a part of the pouch is pre-interlocked with the strip. A strip can be torn away from most of the pouch using another part of the pouch as a handling portion. Also disclosed are methods of making such assemblies, strips obtained from such assemblies, and methods of using such strips to control flying insects.

4 Claims, 3 Drawing Sheets

TOUCHLESS VOLATILE DISPENSER

CROSS REFERENCES TO RELATED APPLICATIONS

Not Applicable

STATEMENT REGARDING FEDERALLY SPONSORED RESEARCH

Not Applicable

BACKGROUND OF THE INVENTION

The present invention relates to devices for dispensing volatiles into the air. It appears to be particularly well suited for controlling flying insects that may be present in building rooms.

The term "volatile medium" is used below to refer to a readily evaporable material having an active ingredient, such as (but not limited to) fragrances, disinfectants, deodorizers and especially insect control actives. The term "active" in this context refers to a material to be released in order to achieve a desired effect (e.g., an insect control active may kill and/or repel insects).

There are a number of examples in the prior art of substrates coated or impregnated with substances. Some of these have previously been stored in a sealed pouch until use. The pouch was torn open at its top edge and the user reached into the pouch to remove the strip. This either required the use of a special tool (e.g. a tweezers) or led to the consumer coming into contact with the substrate.

This could be a safety concern for certain insecticides, thus limiting the choice of actives. Even where contact with human skin was not a safety concern, it could be perceived that way by the consumer.

One dispenser design for use with volatile media was disclosed in U.S. Pat. No. 6,012,643. The disclosure of this patent, and of all other publications referred to herein, are One dispenser design for use with volatile media was disclosed in U.S. Pat. No. 6,012,643. The disclosure of this patent, and of all other publications referred to herein, are incorporated by reference as if fully set forth herein. This patent disclosed a hangable device for dispensing into the air fragrance that was impregnated into a substrate. The substrate was initially enclosed in a type of pouch that had multiple tear-away segments that were removed as needed to meter the release of the fragrance.

While this product extends the useful life of volatile strips, it exposes only a small segment of the strip at a time (which may be less desirable for insecticidal use). Moreover, it requires multiple contacts with the structure.

U.S. Pat. No. 968,237 discloses a strip which acts as a fly catcher. It is coated with a gummy bait substance so as to both bait and trap insects to the strip. It is not designed to emit a volatile as an active, requires the use of an awkward opening mechanism, and in any event leaves the lower portion of its main pouch in place during use (thereby presenting a somewhat ugly product).

Thus, there is a need for a further improved dispensing strip.

BRIEF SUMMARY OF THE INVENTION

In one aspect the invention provides a dispensing strip assembly. It has a vapor impermeable pouch with opposite sides, and a substrate in the form of a strip inside the pouch which is impregnated with a volatile medium. For purposes of this application "impregnated" can mean surface coated or partially or totally permeated with the volatile medium. The opposite sides of the pouch are interlocked with an end of the strip.

In preferred forms, the strip has an opening adjacent its upper end and the pouch is interlocked with the strip through the opening. Also, the pouch has tear points formed at opposed lateral edges below the opening in the strip. When the strip substrate is impregnated with an insect control active, the device can be used to repel and/or kill insects. When the strip substrate is impregnated with a fragrance or perfume, the device can be used as an air freshener, for example, in a closet or automobile.

In another aspect the invention provides a hangable strip for dispensing a volatile medium. There is a strip impregnated with a volatile medium, the strip having adjacent its end an opening. There are also opposite sides of a tear away portion of a vapor impermeable pouch that previously held the strip. They are joined together through the opening in the strip such that the end of the strip is interlocked with the pouch tear away portion. There is also a hanger attached to the strip through the pouch tear away portion.

It will be appreciated from the description below that one can tear the outer pouch of such a dispensing strip assembly at the tear points and then grip and pull firmly up at the upper end of the pouch. This will cause the pouch to tear essentially horizontally below the interlock, albeit without tearing the strip itself. The upper portion of the pouch remains with the strip as a type of handle.

It should be appreciated that the size of the tear notches can be varied depending on the selection of tensile strength and tensile resistance of the substrate and outer pouch. For this purpose, notch sensitive plastic barrier films are preferred for the outer pouch.

One can use the handle to pull out the strip from the bottom part of the pouch. Gravity (sometimes with the assist of a little shaking) will then cause the strip to unfold into a generally vertical strip. A hanger attached to the "handle" prior to tearing open the pouch can then be used to hang the dispensing strip from a closet bar, wall nail, fan housing, or other room structure.

In yet another aspect the invention provides a method of forming such a dispensing strip assembly. One forms a hole in an end of a strip, notches a lateral edge of a pocket to create a tear point, and inserts the strip into the pocket so that a top end of the strip is positioned above the tear point.

One then positions a volatile medium in the pocket so as to impregnate the strip therewith, and seals a top end of the pocket to form a vapor impermeable pouch around the impregnated strip and also so that opposite sides of the pouch are joined together through the strip hole. This interlocks an end of the strip to an end of the pouch.

In yet another form the invention provides methods for controlling flying insects in a room by hanging such a strip in the room.

The present invention permits the long-term stable storage (e.g. at retail stores) of such products. When the product is to be used, most of the pouch may be discarded to expose the strip. Importantly, contact between the hand and active is avoided.

By interlocking one end of the strip to an end of the pouch, one can design an outer pouch that will break cleanly before the strip does. Further, this helps assure that the strip can be completely pulled out of the pouch (notwithstanding being in folded form) without the strip pulling away from the "handle".

The present invention is also well suited for production by automated production techniques. Further, it can be produced at extremely low cost.

These and still other advantages of the invention will appear from the following description. In the description, reference is made to the accompanying drawings which from a part hereof, and in which there is shown by way of illustration a preferred embodiment of the invention.

DETAILED DESCRIPTION OF THE PREFERRED EMBODIMENT

Figure 1:
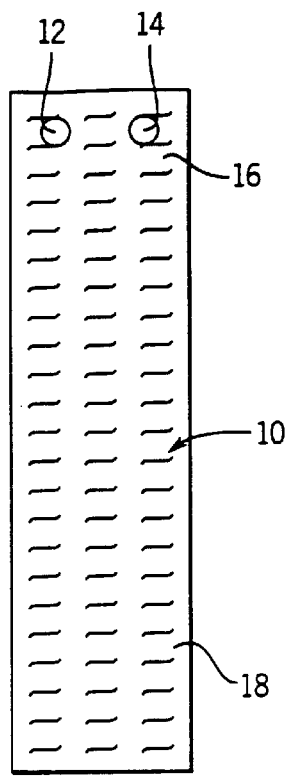
FIG. 1 is a front elevational view of a strip for use in connection with the present invention.
Figure 2:
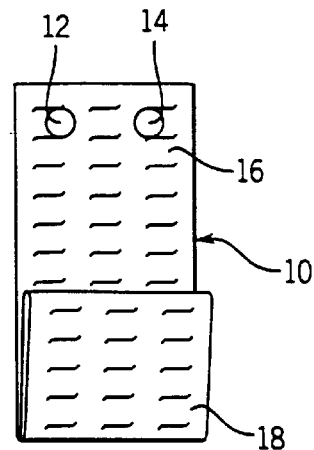
FIG. 2 is frontal, slightly left, perspective view of the strip of FIG. 1, albeit shown with the lower end of the strip folded up.

Referring to FIGS. 1 and 2, the dispensing assembly includes a substrate 10 that is in strip form. It is preferably a flat, somewhat flexible, rectangular card of vegetable fiber, such as wood pulp/paper. However, it could alternatively be made from numerous other synthetic and/or natural materials. For example, in one embodiment we used a non-woven polymer for the strip. This was very absorbent but led to slower release.

Other suitable strip substrates could be wettable films, microporous films, cloths, and other substrates that will release the volatile. Note that the variety of suitable materials is increased because the strip does not need to be compatible to the pouch material for heat sealing.

The strip 10 preferably has a pair of through holes 12 and 14 that are spaced apart at a top end 16. If desired, only one such hole need be used. A bottom end 18 of the strip can be folded up upon itself for storage (see FIG. 2).

Figure 3:
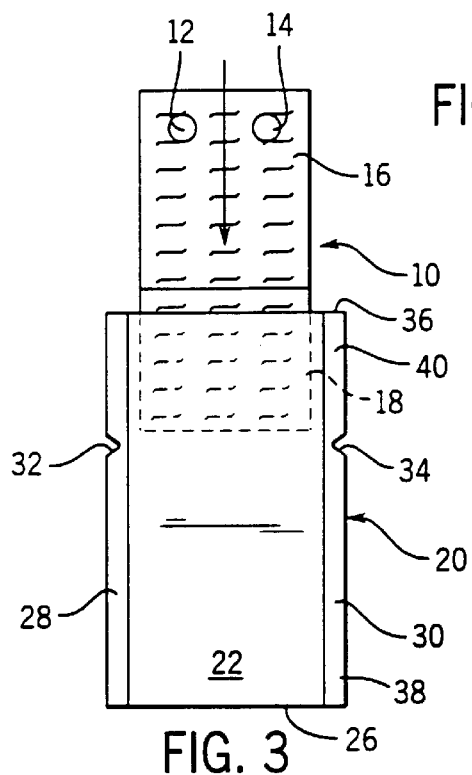
FIG. 3 is a front elevational view (with the pouch shown in section) of the strip of FIG. 2 being inserted into a vapor impermeable pouch.

Referring next to FIG. 3, the folded strip substrate 10 is stored in a vapor impermeable pouch 20, preferably made of a heat sealable material, such as a plastic. One such suitable material is BAREX® brand plastic which is available from BP Amoco. Other suitable plastics for the outside pouch include, without limitation, polyesters/copolyesters, nylon, polypropylene, and various laminations of the preceding materials also including paper, aluminum foil and other sealant materials.

Figure 4:
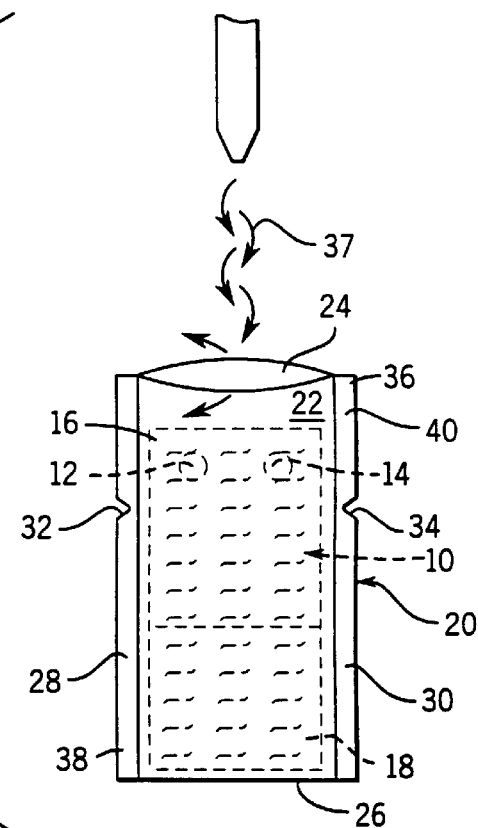
FIG. 4 is a view similar to FIG. 3, albeit with the strip fully inserted and active being shown as being added.
Figure 8:
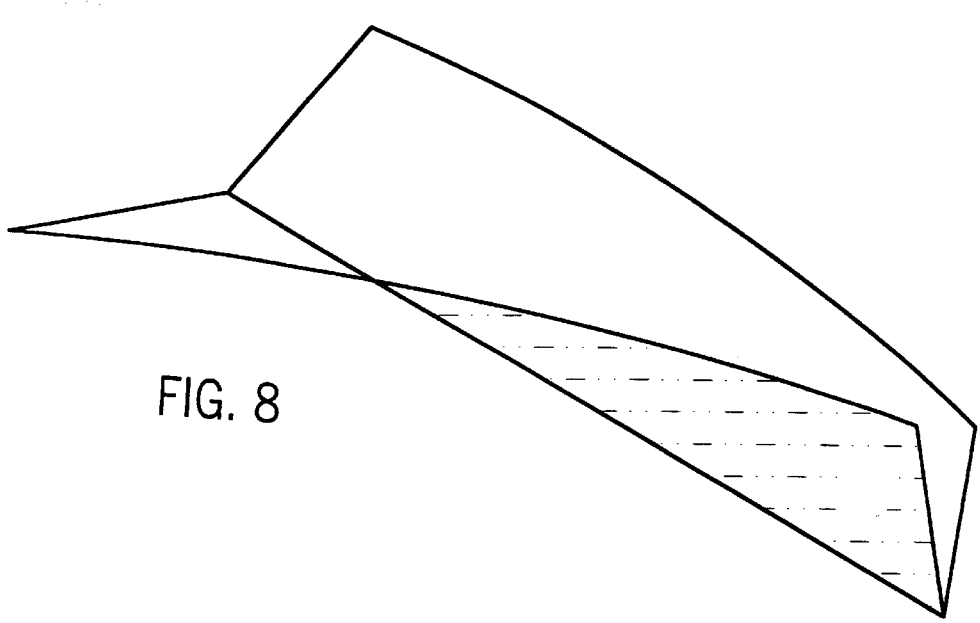
FIG. 8 depicts a film web that is longitudinally folded.

As best seen in FIG. 4, the pouch 20 begins in the form of an upwardly open pocket which has opposite front 22 and back 24 sides. There can be a common bottom 26, and the sides can be joined at lateral edges 28 and 30 by a suitable sealant, such as an adhesive, or sealing process, such as heat sealing or ultrasonic welding. The bottom does not need further sealing if it is a fold line formed of a sheet that is folded back on itself (see FIG. 8). If two separate pieces of plastic are used, the bottom can also be sealed.

The lateral edges 28 and 30 are preferably formed with notches 32 and 34, respectively, at the same distance from a top edge 36 of the pouch 20. This places them below the openings 12 and 14 in the strip substrate 10 when it disposed in the pouch 20. The notches 32 and 34 provide tear-points facilitating tearing the pouch 20 from the lateral edges.

With the strip 10 disposed within the pouch 20, a suitable volatile medium (shown by arrows 37) is dispensed in liquid form into the pocket to impregnate the strip substrate 10. In one embodiment, an insect repellant is added as the active. Pryethrum and pyrethroid type materials commonly now used in mosquito coils are likely to be the most useful for this purpose. Especially preferred pyrethroids (from the standpoint of expense, activity or both vis-a-vis mosquitos) are d-allethrin, allethrin, prallethrin, bioalletherin, s-bioalletherin, esbiol, dichlorvos, transfluthrin, pyrethrum and combinations thereof. Other insect control actives can be used, such as the repellants DEET, citronella, lemon grass oil, lavender oil, cinnamon oil, neem oil, clove oil, sandalwood oil and geraniol as well as the insect growth regulators, such as hydroprene.

The actives will typically be carried in a hydrocarbon solvent such as Isopar or other known solvents that have previously been used to dispense volatile actives from substrates.

The dispensing strips of the present invention can also be used as a disinfectant/fragrancer/deodorizer. A wide variety of such volatiles are well known in the art. The dispensing strip can also dispense multiple actives to, for example, both disinfect and freshen the air.

Figure 5:
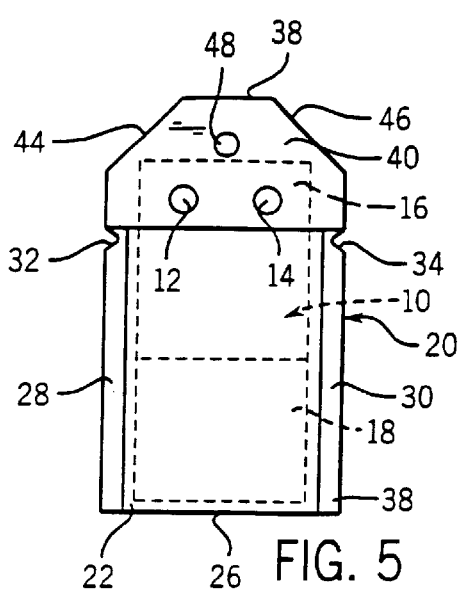
FIG. 5 is a view similar to FIG. 4, albeit at a later stage of manufacture.

To form the FIG. 5 structure from the FIG. 4 structure, one first cuts off triangle pieces from the top (for ornamental reasons) to crate corners 44 and 46. Then, a tear-away top end 40 (above the notches 32 and 34) of the pouch 20 is hermetically heat sealed so that the front 22 and back 24 sides are joined together at the top edge 36. Importantly, the heat sealing also causes the sides 22 and 24 to be joined together through the openings 12 and 14. This interlocks the strip substrate 10 to the tear-away top end 40 of the pouch 20.

One can also provide an additional hole 48 for receiving a hanger 50. This then results in the product that can be stored on a long-term basis.

Figure 6:
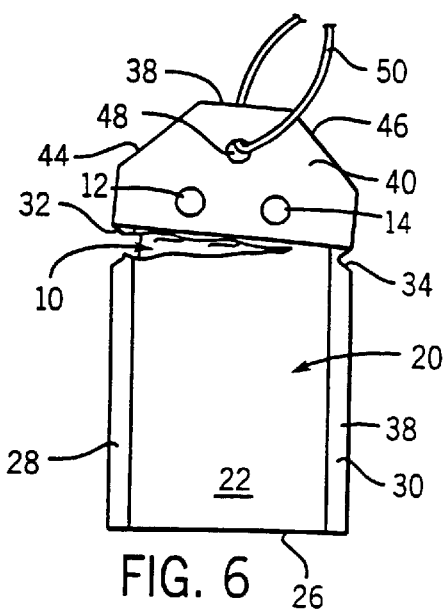
FIG. 6 is a view similar to FIG. 5, albeit with a hanger inserted in a top opening and the pouch in the process of being torn open.
Figure 7:
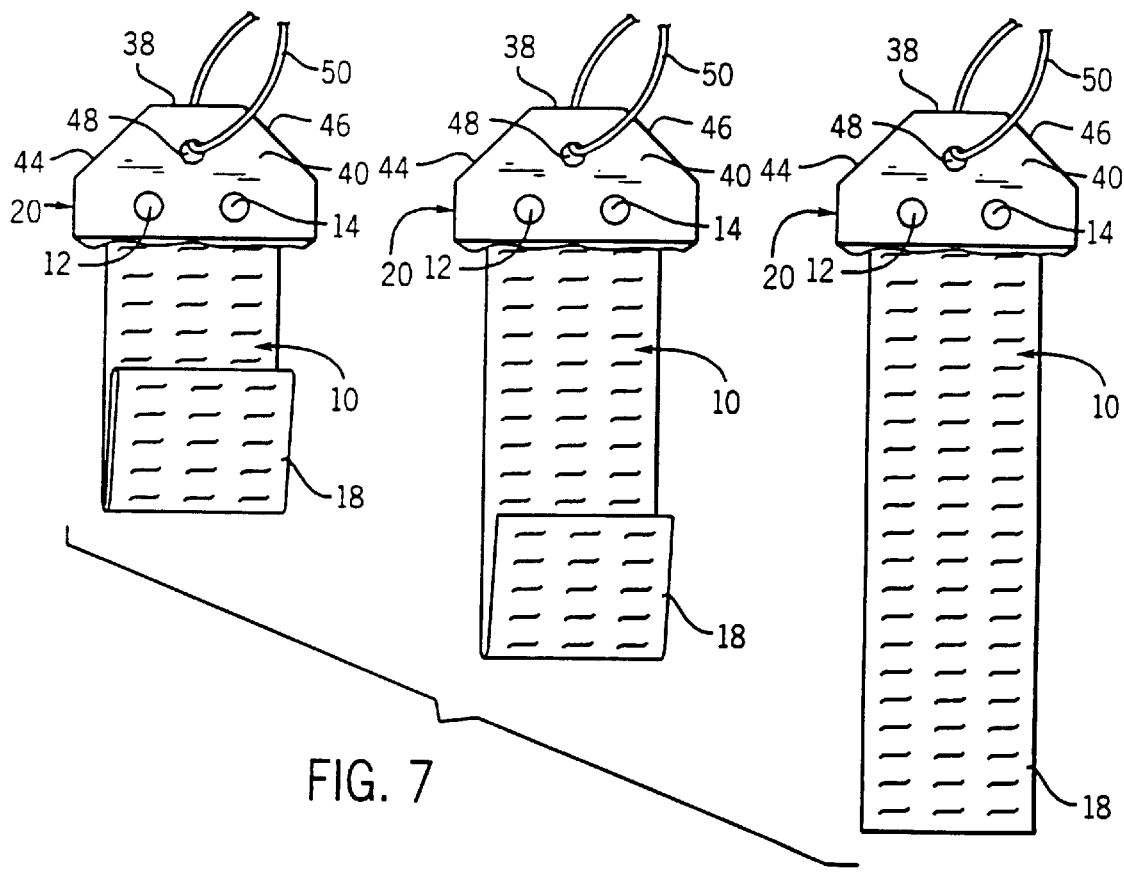
FIG. 7 shows the dispensing strip in various stages of unfolding.

Referring next to FIGS. 6 and 7, the top end 40 of the pouch 20 can be torn away by hand, using the notches 32 and 34 to help start the (and to define the path of) ripping. Once the tear has been made, the strip can be pulled out from a handle portion 38.

The strip 10 will then automatically unfold due to gravity and/or due to a little shaking. See generally FIG. 7. The device can then be hung via hanger 50.

Figure 9:
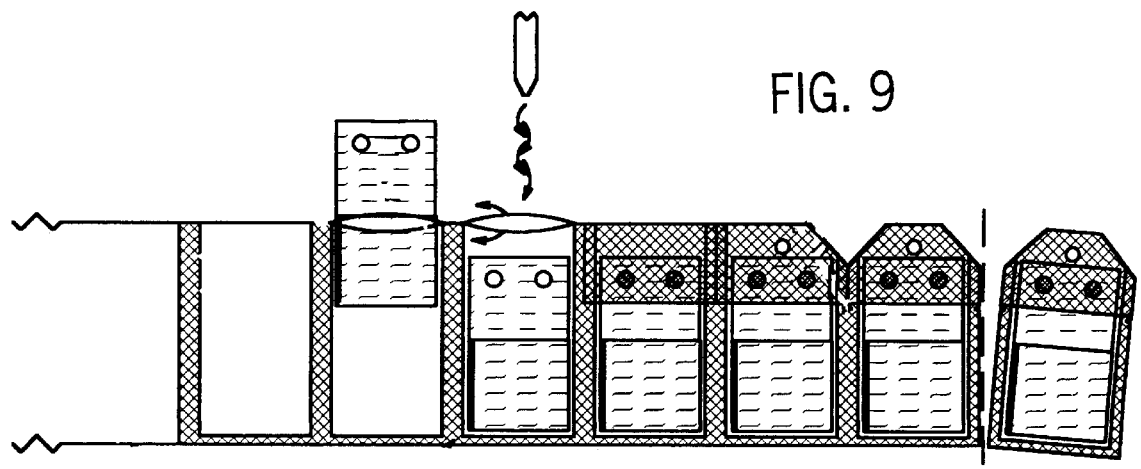
FIG. 9 depicts how the FIG. 8 film web can be processed to form dispensing assemblies of the present invention.

FIG. 9 depicts a preferred production line for forming the dispensing strips. The FIG. 8 folded materials is fed from a web starting at the left. Progressing then left to right, the sides of the pouch are heat sealed, the strip is inserted, the active is added, the upper portion of the pouch is heat sealed, a hanger hole is provided and corners of the upper tab are cut for aesthetics, and each dispensing strip is severed from the other. It will therefore be appreciated that this technology is suitable for high speed automation.

It should be appreciated that other embodiments of the dispenser not mentioned above are within the scope of the invention. For example, the strip need not be folded at all within the pouch. Also, the form of the interlock between the pouch and strip need not be both sides of the pouch sealed together through a through hole. Rather, the interlocking may be achieved through selection of strip and pouch materials that seal to each other. Accordingly, the claims should be referenced in order to determine the full scope of the invention.

INDUSTRIAL APPLICABILITY

The invention provides a hangable strip for dispensing a volatile active. The strip can be stored in a pouch which can be opened in a way where a user is not required to contact the volatile material in order to activate the system.

What is claimed is:

1. A dispensing strip assembly, comprising:
   a vapor impermeable pouch having opposite sides; and
   a substrate in the form of a strip inside the pouch which is impregnated with a volatile medium;
   wherein there is a heat seal between the opposite sides of the pouch through an opening in an end of the substrate to interlock the substrate and the pouch, such that the opposite sides of the pouch extend over and all the way across said opening and are also joined together through the opening by the heat seal, whereby said opposite sides of the pouch completely block the opening; and
   wherein the pouch has a first tear notch formed at a lateral edge, below the opening.

2. The dispensing strip assembly of claim 1, wherein the pouch also has a second tear notch formed at an opposite lateral edge from where the first tear notch is formed, the second tear notch also being below the opening.

3. The dispensing strip assembly of claim 1, wherein the volatile medium is an insect control active.

4. The dispensing strip assembly of claim 1 wherein the volatile medium includes a fragrance.

* * * * *